United States Patent
Fu et al.

(10) Patent No.: US 11,092,999 B2
(45) Date of Patent: Aug. 17, 2021

(54) WEARABLE ELECTRONIC DEVICE AND DISPLAY METHOD OF WEARABLE ELECTRONIC DEVICE

(71) Applicant: Huawei Technologies Co., Ltd., Shenzhen (CN)

(72) Inventors: Jiali Fu, Shenzhen (CN); Maosheng Huang, Shenzhen (CN); Huimin Zhang, Shenzhen (CN); Mingjie Dong, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 16/528,039

(22) Filed: Jul. 31, 2019

(65) Prior Publication Data

US 2019/0354136 A1  Nov. 21, 2019

Related U.S. Application Data

(63) Continuation of application No. 15/177,622, filed on Jun. 9, 2016, now Pat. No. 10,394,279, which is a (Continued)

(30) Foreign Application Priority Data

Dec. 11, 2013  (CN) .......................... 201310676780.7

(51) Int. Cl.
*G06F 1/16* (2006.01)
*A61B 5/021* (2006.01)
(Continued)

(52) U.S. Cl.
CPC .............. *G06F 1/163* (2013.01); *A61B 5/021* (2013.01); *A61B 5/681* (2013.01); *A61B 5/742* (2013.01);
(Continued)

(58) Field of Classification Search
CPC ...... G06F 1/1601; G06F 1/163; G06F 1/1643; G06F 1/1652; G06F 1/169; G06F 1/1694;
(Continued)

(56) References Cited

U.S. PATENT DOCUMENTS 8,663,126 B1 * 3/2014 Al Thalab ............ A61B 5/0823
600/529
2010/0279738 A1  11/2010 Kim
(Continued)

FOREIGN PATENT DOCUMENTS

CN 101776979 A 7/2010
CN 101867637 A 10/2010
(Continued)

*Primary Examiner* — Chun-Nan Lin
(74) *Attorney, Agent, or Firm* — Conley Rose, P.C.

(57) ABSTRACT

A wearable electronic device includes a sensor module, a processor, a display controller, and a display, where the sensor is configured to: collect data, generate a sensor signal that represents a feature of data of currently collected data, and send the sensor signal to the processor, the processor is configured to: determine, according to the received sensor signal, a manner to display that is corresponding to the feature of data represented by the sensor signal and is of the display, generate a display control signal, and send the display control signal to the display controller, and the display controller is configured to control, according to the display control signal, the display to display.

7 Claims, 13 Drawing Sheets

Related U.S. Application Data continuation of application No. PCT/CN2014/085398, filed on Aug. 28, 2014.

(51) Int. Cl.

| | | |
|---|---|---|
| *A61B 5/00* | (2006.01) | |
| *G06F 1/3215* | (2019.01) | |
| *G06F 1/3234* | (2019.01) | |
| *G06F 3/0488* | (2013.01) | |
| *G06F 3/01* | (2006.01) | |
| *G06F 3/041* | (2006.01) | |
| *G06F 3/0484* | (2013.01) | |
| *G06T 11/00* | (2006.01) | |
| *G09G 5/38* | (2006.01) | |
| *A61B 5/01* | (2006.01) | |
| *A61B 5/024* | (2006.01) | |
| *A61B 5/08* | (2006.01) | |
| *A61B 5/145* | (2006.01) | |

(52) U.S. Cl.
CPC ............ *G06F 1/1601* (2013.01); *G06F 1/169* (2013.01); *G06F 1/1643* (2013.01); *G06F 1/1652* (2013.01); *G06F 1/1694* (2013.01); *G06F 1/3215* (2013.01); *G06F 1/3265* (2013.01); *G06F 3/015* (2013.01); *G06F 3/0416* (2013.01); *G06F 3/04845* (2013.01); *G06F 3/04883* (2013.01); *G06F 3/04886* (2013.01); *G06T 11/001* (2013.01); *G09G 5/38* (2013.01); *A61B 5/01* (2013.01); *A61B 5/024* (2013.01); *A61B 5/0816* (2013.01); *A61B 5/14542* (2013.01); *G06F 2203/04806* (2013.01); *G09G 2340/145* (2013.01); *Y02D 10/00* (2018.01)

(58) Field of Classification Search
CPC ................. G06F 1/3215; G06F 1/3265; G06F 2203/04806; G06F 3/015; G06F 3/0416; G06F 3/04845; G06F 3/04883; G06F 3/04886; G06T 11/001; G09G 2340/145; G09G 5/38; A61B 5/681; Y02B 60/1242
See application file for complete search history.

(56) References Cited

U.S. PATENT DOCUMENTS

| | | | |
|---|---|---|---|
| 2011/0157046 A1 | 6/2011 | Lee | |
| 2012/0075168 A1* | 3/2012 | Osterhout | ............... G06F 3/011 345/8 |
| 2012/0253485 A1* | 10/2012 | Weast | ................ A63B 71/0622 700/91 |
| 2013/0044215 A1 | 2/2013 | Rothkopf | |
| 2013/0106684 A1 | 5/2013 | Weast | |
| 2014/0180595 A1* | 6/2014 | Brumback | ............. A63B 24/00 702/19 |
| 2015/0022438 A1 | 1/2015 | Hong | |
| 2015/0113553 A1 | 4/2015 | Pan | |

FOREIGN PATENT DOCUMENTS

| | | |
|---|---|---|
| CN | 102117178 A | 7/2011 |
| CN | 102221873 A | 10/2011 |
| CN | 103212197 A | 7/2013 |
| CN | 103677131 A | 3/2014 |

\* cited by examiner

WEARABLE ELECTRONIC DEVICE AND DISPLAY METHOD OF WEARABLE ELECTRONIC DEVICE

CROSS-REFERENCE TO RELATED APPLICATIONS

This application is a continuation of application Ser. No. 15/177,622 filed on Jun. 9, 2016, which is a continuation of International Patent Application No. PCT/CN2014/085398, filed on Aug. 28, 2014, which claims priority to Chinese Patent Application No. 201310676780.7, filed on Dec. 11, 2013. All of the afore-mentioned patent applications are hereby incorporated by reference in their entireties.

TECHNICAL FIELD

The present disclosure relates to the field of electronic communications, and in particular, to a wearable electronic device and a display method thereof.

BACKGROUND

As electronic technologies rapidly develop, various wearable electronic devices have increasingly diverse functions and are increasingly user-friendly such that a user has better experience in a process of using the wearable electronic devices. Currently, intelligent handheld wearable electronic devices gradually become a trend. For example, many handheld devices that have a shape similar to a wristwatch have been launched, and a user can wear these devices around the wrist, which is convenient for use.

However, a wearable electronic device generally has a relatively small screen. Related content displayed on the relatively small screen is not intuitive, and operations are relatively complex during content display. For example, when vital sign data (temperature, heartbeat, blood pressure, and the like) is checked using the wearable electronic device, the user needs to turn on the display screen of the wearable electronic device to view the vital sign data and determine whether the vital sign data is normal. It is not convenient for special groups of people, such as the old people, to use the wearable electronic device. For example, when the display screen of the device is relatively small, it is extremely difficult for the old people to view clearly related display content. Therefore, it is very necessary to provide a wearable electronic device on which display content can be easily identified.

SUMMARY

Embodiments of the present disclosure provide a wearable electronic device and a display method thereof such that when a display screen of the device is relatively small, related display content can be clearly and easily viewed, and operations are easy and convenient.

According to a first aspect, an embodiment of the present disclosure provides a wearable electronic device, where the wearable electronic device includes a sensor, a processor, a display controller, and a display, where the sensor is configured to collect data, generate a sensor signal that represents a feature of data of currently collected data, and send the sensor signal to the processor, the processor is configured to determine, according to the received sensor signal, a manner to display that is corresponding to the feature of data represented by the sensor signal and is of display content displayed by the display, generate a display control signal, and send the display control signal to the display controller, the display controller is configured to control, according to the display control signal sent by the processor, the display to display the display content in the manner to display, and the display is configured to display the display content.

With reference to the first aspect, in a first possible implementation manner, the sensor is a vital sign sensor, and the display includes an electrochromic housing, where the vital sign sensor is configured to collect vital sign data of a user, generate the sensor signal that represents the vital sign data of the user, and send the sensor signal to the processor, the processor is configured to receive the sensor signal, determine, according to a correspondence between a parameter level of vital sign data and a display color of the electrochromic housing, a color that is corresponding to the current vital sign data and should be displayed by the electrochromic housing, and generate a color display control signal and send the color display control signal to the display controller, and the display controller is configured to control, according to the color display control signal sent by the processor, the electrochromic housing to display the color corresponding to the current vital sign data.

With reference to the first possible implementation manner of the first aspect, in a second possible implementation manner, the electrochromic housing includes at least one different controllable electrochromic area, where different controllable electrochromic areas are corresponding to different types of vital sign data of the user.

With reference to the first aspect, in a third possible implementation manner, the sensor is a horizontal sensor or a gravity sensor, and the display includes a display screen that surrounds the entire wearable electronic device, where the horizontal sensor or the gravity sensor is configured to collect device status data, acquire a position of a highest horizontal point of the wearable electronic device, generate the sensor signal that represents the position of the highest horizontal point of the wearable electronic device, and send the sensor signal to the processor, the processor is configured to receive the sensor signal, determine a display position on the display screen according to an area, on the wearable electronic device, in which the position of the highest horizontal point of the wearable electronic device is located, generate a display control signal that controls the display screen to display at the display position, and send the display control signal to the display controller, and the display controller is configured to control, according to the display control signal sent by the processor, the display screen to display the content at the display position.

With reference to the third possible implementation manner of the first aspect, in a fourth possible implementation manner, the processor is configured to determine, according to the received sensor signal, whether the position of the highest horizontal point of the wearable electronic device is located within a preset display area, and if yes, use a display area whose center is the highest horizontal point as the display position on the display screen, generate a display control signal, and send the display control signal to the display controller, or if no, use a display area whose uppermost end is the highest horizontal point as the display position on the display screen, generate a display control signal, and send the display control signal to the display controller.

With reference to the first aspect, in a fifth possible implementation manner, the sensor is a touch sensor, and the display includes a display screen in a standby state, where the touch sensor is configured to collect operation data of a user, acquire a tapping position of the user on the display screen that is in the standby state, generate the sensor signal that represents the tapping position, and send the sensor signal to the processor, the processor is configured to receive the sensor signal, determine, according to the current tapping position, a lighted area on the display screen that is in the standby state, generate a display control signal that controls the display screen that is in the standby state to display the lighted area, and send the display control signal to the display controller, and the display controller is configured to control, according to the display control signal sent by the processor, the display screen that is in the standby state to display the lighted area.

With reference to the fifth possible implementation manner of the first aspect, in a sixth possible implementation manner, the processor is configured to determine, according to the received sensor signal, whether the current tapping position is located within a display sub-area on the display screen that is in the standby state, where the display sub-area is obtained by dividing the display screen that is in the standby state from a center to two sides by a fixed display area size, and if yes, use a display sub-area in which the current tapping position is located as the lighted area, generate a display control signal, and send the display control signal to the display controller, or if no, use a display sub-area adjacent to the current tapping position as the lighted area, generate a display control signal, and send the display control signal to the display controller.

With reference to the sixth possible implementation manner of the first aspect, in a seventh possible implementation manner, the display is further configured to zoom in, using the tapping position as a center, the lighted area outwards to a preset area range or an area range that adapts to a size of the display screen, zoom in, using a horizontal line in which the tapping position is located as a top, the lighted area downwards to a preset area range or an area range that adapts to a size of the display screen, or zoom in, using a horizontal line in which the tapping position is located as a bottom, the lighted area upwards to a preset area range or an area range that adapts to a size of the display screen.

With reference to the first aspect, in an eighth possible implementation manner, the processor is further configured to determine, according to a current application used on the wearable electronic device, an area of interest that a user intends to focus on or an operation area in which a user needs to perform an operation, generate a full-screen display control signal for displaying in full screen the area of interest or the operation area, and send the full-screen display control signal to the display controller, and the display controller is further configured to control, according to the full-screen display control signal sent by the processor, the display to display in full screen the area of interest or the operation area.

With reference to the first aspect, in a ninth possible implementation manner, the processor is further configured to acquire applications (APPs) used by a user, and sort the APPs in descending order by frequency of use to obtain sorted APPs, add icons corresponding to the first N APPs of the sorted APPs to a display menu, and delete the last M APPs of the sorted APPs to obtain a display menu of a home screen, and generate a display control signal for displaying the display menu of the home screen, and send the display control signal to the display controller, and the display controller is further configured to control, according to the display control signal that is for displaying the display menu of the home screen and sent by the processor, the display to display the display menu of the home screen.

According to a second aspect, a display method of a wearable electronic device is provided, including collecting data, and generating a sensor signal that represents a feature of data of currently collected data, and determining, according to the sensor signal, a manner to display that is corresponding to the feature of data represented by the sensor signal and is of display content, and displaying the display content in the manner to display.

With reference to the second aspect, in a first possible implementation manner, the collecting data, and generating a sensor signal that represents a feature of data of currently collected data includes collecting vital sign data of a user using a vital sign sensor, and generating a sensor signal that represents the vital sign data of the user, and the determining a manner to display that is corresponding to the feature of data represented by the sensor signal and is of display content, and displaying the display content in the manner to display includes determining, according to a correspondence between a parameter level of vital sign data and a display color of an electrochromic housing, a color that is corresponding to the current vital sign data and should be displayed by the electrochromic housing, and generating a color display control signal, and controlling, according to the color display control signal, the electrochromic housing to display the color corresponding to the current vital sign data.

With reference to the first possible implementation manner of the second aspect, in a second possible implementation manner, before the determining a manner to display that is corresponding to the feature of data represented by the sensor signal and is of display content, the method further includes setting a correspondence between at least one different controllable electrochromic area included by the electrochromic housing and different types of vital sign data of the user, where different controllable electrochromic areas are corresponding to different types of vital sign data of the user.

With reference to the second aspect, in a third possible implementation manner, the collecting data, and generating a sensor signal that represents a feature of data of currently collected data includes collecting device status data using a horizontal sensor or a gravity sensor, acquiring a position of a highest horizontal point of a wearable electronic device, and generating a sensor signal that represents the position of the highest horizontal point of the wearable electronic device, and the determining a manner to display that is corresponding to the feature of data represented by the sensor signal and is of display content, and displaying the display content in the manner to display includes determining a display position on the display screen according to an area, on the wearable electronic device, in which the position of the highest horizontal point of the wearable electronic device is located, generating a display control signal that controls the display screen to display at the display position, and controlling, according to the display control signal, the display screen to display the display content at the display position.

With reference to the third possible implementation manner of the second aspect, in a fourth possible implementation manner, the determining a display position on the display screen according to an area, on the wearable electronic device, in which the position of the highest horizontal point of the wearable electronic device is located includes determining whether the position of the highest horizontal point of the wearable electronic device is located within a preset display area, and if yes, using a display area whose center is the highest horizontal point as the display position on the display screen, or if no, using a display area whose uppermost end is the highest horizontal point as the display position on the display screen.

With reference to the second aspect, in a fifth possible implementation manner, the collecting data, and generating a sensor signal that represents a feature of data of currently collected data includes collecting operation data of a user using a touch sensor, acquiring a tapping position of the user on a display screen that is in a standby state, and generating a sensor signal that represents the tapping position, and the determining a manner to display that is corresponding to the feature of data represented by the sensor signal and is of display content, and displaying the display content in the manner to display includes determining, according to the current tapping position, a lighted area on the display screen that is in the standby state, generating a display control signal that controls the display screen that is in the standby state to display the lighted area, and controlling, according to the display control signal, the display screen that is in the standby state to display the lighted area.

With reference to the fifth possible implementation manner of the second aspect, in a sixth possible implementation manner, the determining, according to the current tapping position, a lighted area on the display screen that is in the standby state includes determining whether the current tapping position is located within a display sub-area on the display screen that is in the standby state, where the display sub-area is obtained by dividing the display screen that is in the standby state from the center to two sides by a fixed display area size, and if yes, using a display sub-area in which the current tapping position is located as the lighted area, or if no, using a display sub-area adjacent to the current tapping position as the lighted area.

With reference to the sixth possible implementation manner of the second aspect, in a seventh possible implementation manner, after the determining a lighted area on the display screen that is in the standby state, the method further includes zooming in, using the tapping position as a center, the lighted area outwards to a preset area range or an area range that adapts to a size of the display screen, zooming in, using a horizontal line in which the tapping position is located as a top, the lighted area downwards to a preset area range or an area range that adapts to a size of the display screen, or zooming in, using a horizontal line in which the tapping position is located as a bottom, the lighted area upwards to a preset area range or an area range that adapts to a size of the display screen.

With reference to the second aspect, in an eighth possible implementation manner, the determining a manner to display that is corresponding to the feature of data represented by the sensor signal and is of display content, and displaying the display content in the manner to display includes determining, according to a current application used on a wearable electronic device, an area of interest that a user intends to focus on or an operation area in which a user needs to perform an operation, generating a full-screen display control signal for displaying in full screen the area of interest or the operation area, and displaying in full screen the area of interest or the operation area according to the full-screen display control signal.

With reference to the second aspect, in a ninth possible implementation manner, the determining a manner to display that is corresponding to the feature of data represented by the sensor signal and is of display content, and displaying the display content in the manner to display includes acquiring applications APPs used by a user, and sorting the APPs in descending order by frequency of use to obtain sorted APPs, adding icons corresponding to the first N APPs of the sorted APPs to a display menu, and deleting the last M APPs of the sorted APPs to obtain a display menu of a home screen, generating a display control signal for displaying the display menu of the home screen, and displaying the display menu of the home screen according to the display control signal.

According to a third aspect, a method for displaying vital sign data by a wearable electronic device is provided, including collecting vital sign data of a user using a vital sign sensor, determining, according to a correspondence between a parameter level of vital sign data and a display color of an electrochromic housing, a color that is corresponding to the current vital sign data and should be displayed by the electrochromic housing, and generating a color display control signal, and controlling, according to the color display control signal, the electrochromic housing to display the color corresponding to the current vital sign data.

With reference to the third aspect, in a first possible implementation manner, before the determining a manner to display that is corresponding to the feature of data represented by the sensor signal and is of display content, the method further includes setting a correspondence between at least one different controllable electrochromic area included by the electrochromic housing and different types of vital sign data of the user, where different controllable electrochromic areas are corresponding to different types of vital sign data of the user.

According to a fourth aspect, a display method of a wearable electronic device is provided, including collecting device status data using a horizontal sensor or a gravity sensor, and acquiring a position of a highest horizontal point of a wearable electronic device, determining a display position on the display screen according to an area, on the wearable electronic device, in which the position of the highest horizontal point of the wearable electronic device is located, generating a display control signal that controls the display screen to display at the display position, and controlling, according to the display control signal, the display screen to display content at the display position.

With reference to the fourth aspect, in a first possible implementation manner, the determining a display position on the display screen according to an area, on the wearable electronic device, in which the position of the highest horizontal point of the wearable electronic device is located includes determining whether the position of the highest horizontal point of the wearable electronic device is located within a preset display area, and if yes, using a display area whose center is the highest horizontal point as the display position on the display screen, or if no, using a display area whose uppermost end is the highest horizontal point as the display position on the display screen.

According to a fifth aspect, a display method of a wearable electronic device is provided, including collecting operation data of a user using a touch sensor, and acquiring a tapping position of the user on a display screen that is in a standby state, determining, according to the current tapping position, a lighted area on the display screen that is in the standby state, generating a display control signal that controls the display screen that is in the standby state to display the lighted area, and controlling, according to the display control signal, the display screen that is in the standby state to display the lighted area.

With reference to the fifth aspect, in a first possible implementation manner, the determining, according to the current tapping position, a lighted area on the display screen that is in the standby state includes determining whether the current tapping position is located within a display sub-area on the display screen that is in the standby state, where the display sub-area is obtained by dividing the display screen that is in the standby state from the center to two sides by a fixed display area size, and if yes, using a display sub-area in which the current tapping position is located as the lighted area, or if no, using a display sub-area adjacent to the current tapping position as the lighted area.

With reference to the first possible implementation manner of the fifth aspect, in a second possible implementation manner, after the determining a lighted area on the display screen that is in the standby state, the method further includes zooming in, using the tapping position as a center, the lighted area outwards to a preset area range or an area range that adapts to a size of the display screen, zooming in, using a horizontal line in which the tapping position is located as a top, the lighted area downwards to a preset area range or an area range that adapts to a size of the display screen, or zooming in, using a horizontal line in which the tapping position is located as a bottom, the lighted area upwards to a preset area range or an area range that adapts to a size of the display screen.

According to a sixth aspect, a display method of a wearable electronic device is provided, including determining, according to a current application used on a wearable electronic device, an area of interest that a user intends to focus on or an operation area in which a user needs to perform an operation, generating a full-screen display control signal for displaying in full screen the area of interest or the operation area, and displaying in full screen the area of interest or the operation area according to the full-screen display control signal.

According to a seventh aspect, a display method of a wearable electronic device is provided, including acquiring applications APPs used by a user, and sorting the APPs in descending order by frequency of use to obtain sorted APPs, adding icons corresponding to the first N APPs of the sorted APPs to a display menu, and deleting the last M APPs of the sorted APPs to obtain a display menu of a home screen, generating a display control signal for displaying the display menu of the home screen, and displaying the display menu of the home screen according to the display control signal.

According to the wearable electronic device and the display method thereof that are provided in the embodiments of the present disclosure, a processor can determine, according to a received sensor signal, a manner to display corresponding to a feature of data represented by the sensor signal, and generate a display control signal, and a display controller controls, according to the display control signal, a display to display correspondingly. That is, in the present application, different manner to displays can be determined according to different feature of datas, and a manner to display has flexibility such that a user can view clearly and easily display content related to a current feature of data.

DESCRIPTION OF EMBODIMENTS

The following clearly describes the technical solutions in the embodiments of the present disclosure with reference to the accompanying drawings in the embodiments of the present disclosure. Apparently, the described embodiments are merely some but not all of the embodiments of the present disclosure. All other embodiments obtained by persons of ordinary skill in the art based on the embodiments of the present disclosure without creative efforts shall fall within the protection scope of the present disclosure.

Figure 1:
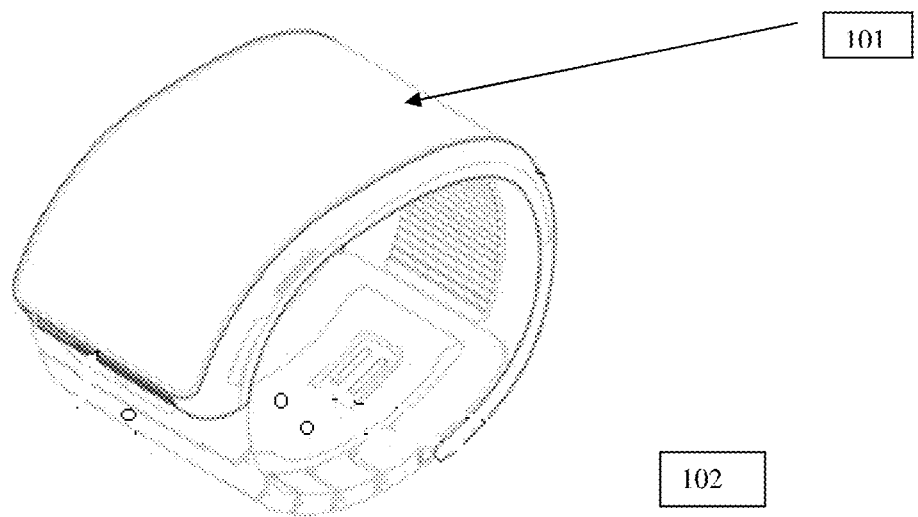
FIG. 1 is a schematic diagram of a wristwatch-shaped wearable electronic device involved in an embodiment of the present disclosure.
Figure 2:
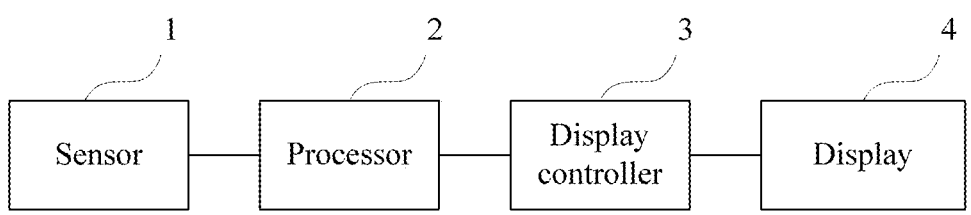
FIG. 2 is a schematic diagram of a composition structure of a wearable electronic device according to an embodiment of the present disclosure.

Based on a wristwatch-shaped wearable electronic device shown in FIG. 1, an embodiment of the present disclosure provides a wearable electronic device. A composition structure of the wearable electronic device is shown in FIG. 2, and the wearable electronic device includes a sensor 1, a processor 2, a display controller 3, and a display 4, where the sensor 1 is configured to collect data, generate a sensor signal that represents a feature of data of currently collected data, and send the sensor signal to the processor 2, the processor 2 is configured to determine, according to the received sensor signal, a manner to display that is corresponding to the feature of data represented by the sensor signal and is of related display content displayed by the display 4, generate a display control signal, and send the display control signal to the display controller 3, the display controller 3 is configured to control, according to the display control signal sent by the processor 2, the display 4 to display the related display content in the determined manner to display, and the display 4 is configured to display the related content in the determined manner to display.

In an embodiment, the sensor 1 in this embodiment of the present disclosure may be different sensors for collecting different data. For example, one or more vital sign sensors may be disposed, and vital sign data of different types, such as temperature, blood pressure, blood oxygen, heartbeat, breath, and a pulse, of a user is collected using the vital sign sensor, or a horizontal sensor and/or a gravity sensor may be disposed to collect device status data of the wearable device, for example, a position of a highest horizontal point of the wearable device is determined, or a touch sensor is disposed and configured to collect a touch position of the user. Data is collected using different sensors, each sensor generates a sensor signal that represents a feature of data of currently collected data, and sends the sensor signal to the processor 2. The processor 2 receives the sensor signal that represents the feature of data of currently collected data and is sent by each sensor, determines, according to the sensor signal, a manner to display that is corresponding to a feature of data represented by each sensor signal and is of the display 4, generates a corresponding display control signal, and sends the display control signal to the display controller 3. The display controller 3 controls, according to the display control signal, the display 4 to display.

Further, the display 4 in this embodiment of the present disclosure includes an electrochromic housing and a display screen. When being displayed, related content may be displayed using the housing of the wearable electronic device, or may be displayed using the display screen of the wearable electronic device.

The housing of the wearable electronic device in this embodiment of the present disclosure is preferably an electrochromic housing, and the electrochromic housing is made of an electrochromic material. Driven by different voltages, the electrochromic material generates different colors, and implements a color change. A voltage within −2 V to +2 V only needs to be applied, which is suitable for implementation on a type of a low-working-voltage device, such as the wearable electronic device. In this embodiment of the present disclosure, different control signals are generated according to different feature data of a user who wears the wearable electronic device to control the electrochromic housing of the wearable electronic device to display different colors, and different colors represent different vital sign data, that is, different health statuses. Wearers may directly learn their own physical condition according to a color displayed by the housing of the wearable electronic device.

In this embodiment of the present disclosure, the display screen of the wearable electronic device may be an arc-shaped flexible screen that surrounds the entire wearable electronic device, or may be a flat screen that is disposed in a partial area of the wearable electronic device. A manner to display of the display screen may be displaying in full screen, or may be displaying in a partial area of the screen. In addition, when related content is displayed, all content may be displayed, or partial content may be displayed. Furthermore, displayed content may further be displayed in full screen or displayed by means of zooming in.

With reference to specific application scenarios, the following embodiments of the present disclosure describe in detail different manner to displays that are corresponding to different data and are of the wearable device in this embodiment of the present disclosure.

Embodiment 1

In Embodiment 1 of the present disclosure, a sensor 1 is a vital sign sensor, and a display 4 includes an electrochromic housing. The vital sign sensor can collect vital sign data of a user, generate a sensor signal that represents the vital sign data of the user, and send the sensor signal to a processor 2. The processor 2 can obtain a color display solution of the electrochromic housing according to a preset rule by matching, generate a color display control signal, and send the color display control signal to a display controller 3. The display controller 3 controls a hardware circuit to output different control voltages, and further controls the electrochromic housing to display a color corresponding to the current vital sign data.

Figure 3:
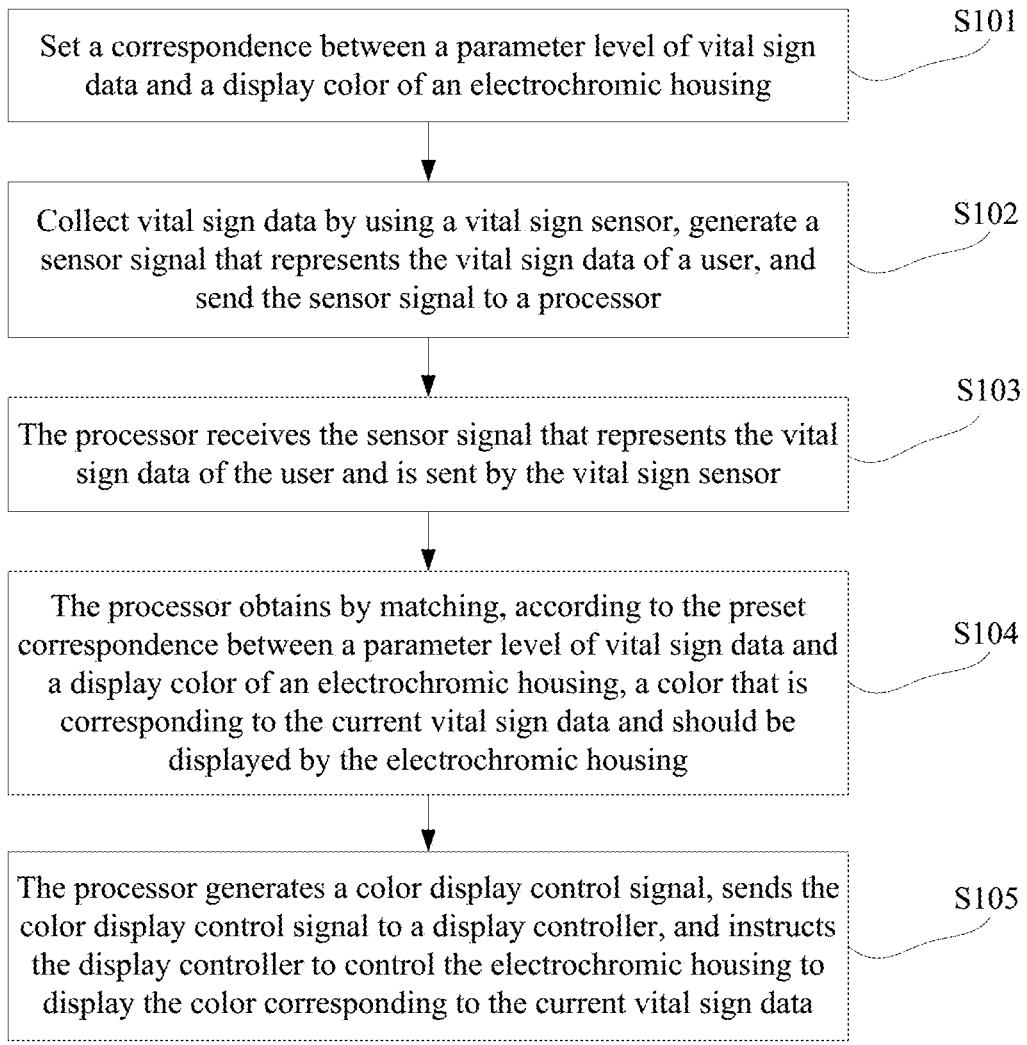
FIG. 3 is a schematic flowchart of displaying vital sign data by a wearable electronic device according to an embodiment of the present disclosure.

In an embodiment, an implementation process of displaying a color according to collected vital sign data in this embodiment of the present disclosure is shown in FIG. 3, and includes the following steps.

S101: Set a correspondence between a parameter level of vital sign data and a display color of an electrochromic housing.

In this embodiment of the present disclosure, the vital sign data includes but is not limited to temperature data, blood pressure data, heartbeat data, blood oxygen data, breath data, and pulse data. A user may set a relationship between a parameter level of each vital sign data and a display color of the electrochromic housing. The temperature data and the blood pressure data are used as examples. A preset correspondence shown in the following Table 1 may be set for a temperature parameter level and a display color of the electrochromic housing, and a preset correspondence shown in the following Table 2 may be set for a blood pressure parameter level and a display color of the electrochromic housing.

TABLE 1

| Temperature parameter level | Display color of a housing | Health level |
| --- | --- | --- |
| 36.5-37° C. | Green (or a natural color) | Normal |
| 37-37.5° C. | Yellow | Close to or equal to a health critical value, have a healthy diet and a good rest |
| 37.5-38° C. | Orange | Exceed the health critical value, and take medicine for prevention |
| 38-39° C. | Red | Dangerous, hospitalize for treatment |
| >39° C. | Black | Highly dangerous, an immediate rescue is needed |

TABLE 2

| Range of blood pressure data (unit: mmHg) | Color of a housing | Health level |
| --- | --- | --- |
| 90 < systolic pressure <140 and 60 < diastolic pressure < 90 | Green (or a natural color) | Normal |
| 160 > systolic pressure ≥140 and (or) 95 > diastolic pressure ≥ 90 | Yellow | Borderline hypertension |
| Systolic pressure ≥ 160 and (or) diastolic pressure ≥ 95 | Red | Severe hypertension |
| Systolic pressure ≤ 90 and (or) diastolic pressure ≤ 60 | Orange | Hypotension |

Further, the electrochromic housing in this embodiment of the present disclosure may include at least one different controllable electrochromic area, where different controllable electrochromic areas are corresponding to different types of vital sign data of the user, and each controllable electrochromic area can be independently controlled.

In this embodiment of the present disclosure, several different blocks may be set on the electrochromic housing, and different blocks are corresponding to different types of vital sign data. A corresponding color is separately set for a parameter level of each type of vital sign data. For example, a first block is used to display temperature, and a second block is used to display blood pressure. In addition, a preset relationship between a temperature parameter level and a display color of the electrochromic housing may be shown in Table 1, and a preset relationship shown in Table 2 may be set for a blood pressure parameter level and a display color of the electrochromic housing.

It should be noted that setting of the correspondence between a parameter level of vital sign data and a display color of an electrochromic housing is not limited to methods shown in Table 1 and Table 2. For example, a level may be set, and a preset range is set. When the parameter level of the vital sign data exceeds the preset range, a color is displayed to remind the user.

S102: Collect vital sign data using a vital sign sensor, generate a sensor signal that represents the vital sign data of a user, and send the sensor signal to a processor 2.

S103: The processor 2 receives the sensor signal that represents the vital sign data of the user and is sent by the vital sign sensor.

S104: The processor 2 determines, according to the correspondence between a parameter level of vital sign data and a display color of an electrochromic housing in S101, a color that is corresponding to the current vital sign data and should be displayed by the electrochromic housing.

S105: The processor 2 generates a color display control signal, sends the color display control signal to a display controller 3, and instructs the display controller 3 to control the electrochromic housing to display the color corresponding to the current vital sign data.

In this embodiment of the present disclosure, the sensor 1 is configured to collect vital sign data of a user using a vital sign sensor, generate a sensor signal that represents the vital sign data of the user, and send the sensor signal to the processor 2, the processor 2 is configured to receive the sensor signal that represents the vital sign data of the user and is sent by the sensor 1, determine, according to a correspondence between a parameter level of vital sign data and a display color of an electrochromic housing, a color that is corresponding to the current vital sign data and should be displayed by the electrochromic housing, and generate a color display control signal and send the color display control signal to the display controller 3, and the display controller 3 is configured to control, according to the color display control signal sent by the processor 2, the electrochromic housing to display the color corresponding to the current vital sign data, where the display controller 3 may control, according to the color display control signal sent by the processor 2, a hardware circuit to output control voltage, and drive the electrochromic housing to display a corresponding color.

Further, in a process in which a wearable electronic device in this embodiment of the present disclosure displays a color according to collected vital sign data and using the electrochromic housing, a corresponding prompt tone may be set, or the vital sign data is sent to a related person or a medical center in real time to better plays a prompt function.

Still further, a switch may be disposed in this embodiment of the present disclosure, which is used for the user to select whether to enable a function of displaying different colors using the electrochromic housing. If the function is not enabled, the housing of the electrochromic housing displays a normal color, and does not change a color. If the function is enabled, a sensor module of the wearable electronic device collects vital sign data of the user in real time using the vital sign sensor, the processor processes the collected vital sign data, and outputs a corresponding color control signal, and the display controller controls the housing of the electrochromic housing to display different colors according to different vital sign data to remind the user of a physical condition such that the user is reminded and takes corresponding preventive measures in time.

According to the foregoing method for displaying vital sign data in this embodiment of the present disclosure, related content can be displayed using an electrochromic housing of a wearable electronic device and can be intuitively displayed. In addition, a user does not need to turn on a display, which is more convenient for use.

Embodiment 2

A wearable electronic device has an arc-shaped display screen, and is easily shifted in a wearing process of a user. In this embodiment of the present disclosure, a sensor 1 is set as a horizontal sensor or a gravity sensor, and a display 4 includes a display screen (which may provide a display function at all positions of the wearable electronic device) that surrounds the entire wearable electronic device. A position of a highest horizontal point of the wearable electronic device is acquired using the horizontal sensor or the gravity sensor, therefore, a display position on the display screen of the wearable electronic device is determined such that the display position on the display screen is located at an uppermost end of the wearable electronic device, which is convenient for the user to view related content.

In an embodiment, the horizontal sensor or the gravity sensor may determine a tilt angle of the device relative to a horizontal plane by measuring a change of a static gravity acceleration, and further can collect device status data of the wearable electronic device, and acquire the position of the highest horizontal point of the wearable electronic device when the wearable electronic device is being used. The display position on the display screen may be determined according to an area, on the wearable electronic device, in which the position of the highest horizontal point of the wearable electronic device is located.

Figure 4:
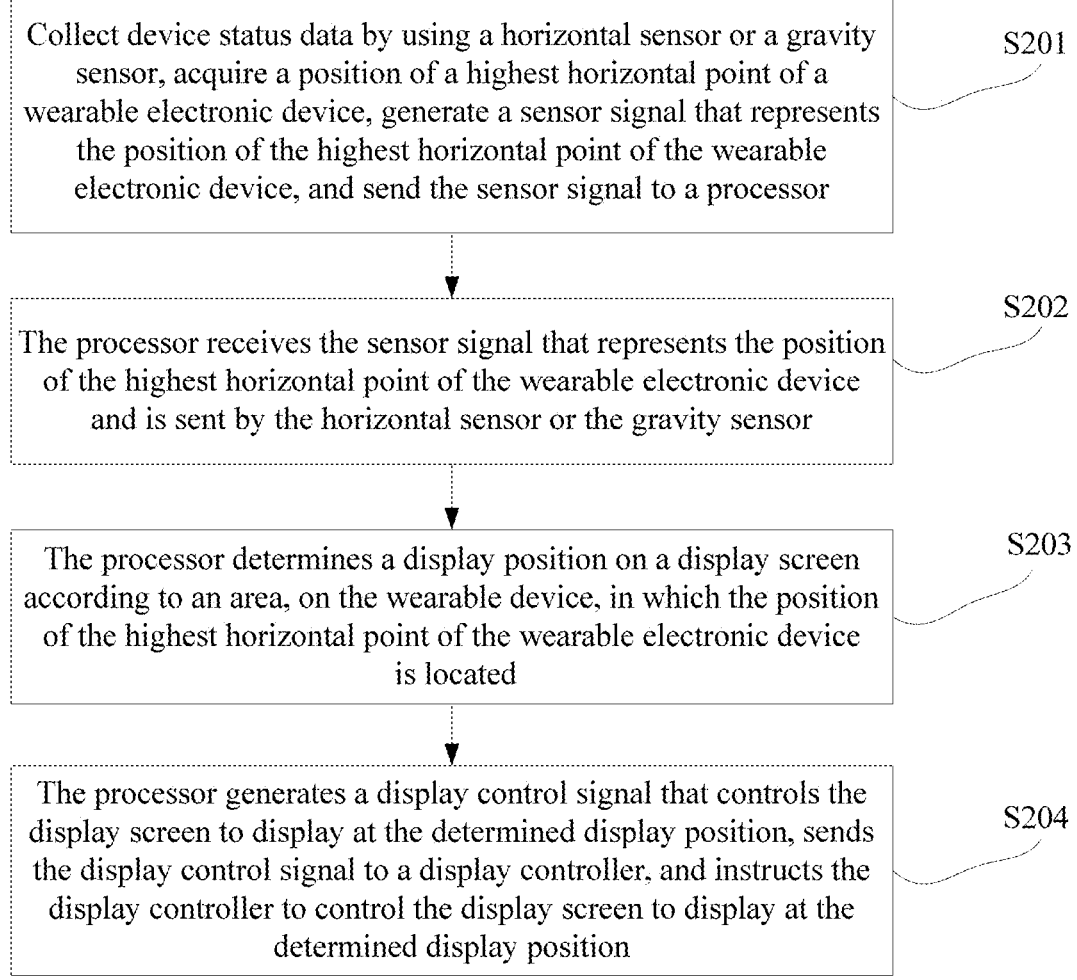
FIG. 4 is a schematic diagram of a process of determining a display position on a display screen of a wearable electronic device according to an embodiment of the present disclosure.

A process of determining the display position on the display screen of the wearable electronic device in this embodiment of the present disclosure is shown in FIG. 4, and includes the following steps.

S201: Collect device status data using a horizontal sensor or a gravity sensor, acquire a position of a highest horizontal point of a wearable electronic device, generate a sensor signal that represents the position of the highest horizontal point of the wearable electronic device, and send the sensor signal to a processor 2.

In an embodiment, a sensor (the horizontal sensor or the gravity sensor) that can measure levelness of the device is disposed in a sensor 1 of the wearable electronic device in this embodiment of the present disclosure. For example, a level vial may be used to detect a change of the position of the highest horizontal point of the wearable electronic device in real time, and send the sensor signal that represents the position of the highest horizontal point of the wearable electronic device to the processor 2.

S202: The processor 2 receives the sensor signal that represents the position of the highest horizontal point of the wearable electronic device and is sent by the horizontal sensor or the gravity sensor.

S203: The processor 2 determines a display position on a display screen according to an area, on the wearable device, in which the position of the highest horizontal point of the wearable electronic device is located.

Figure 5:
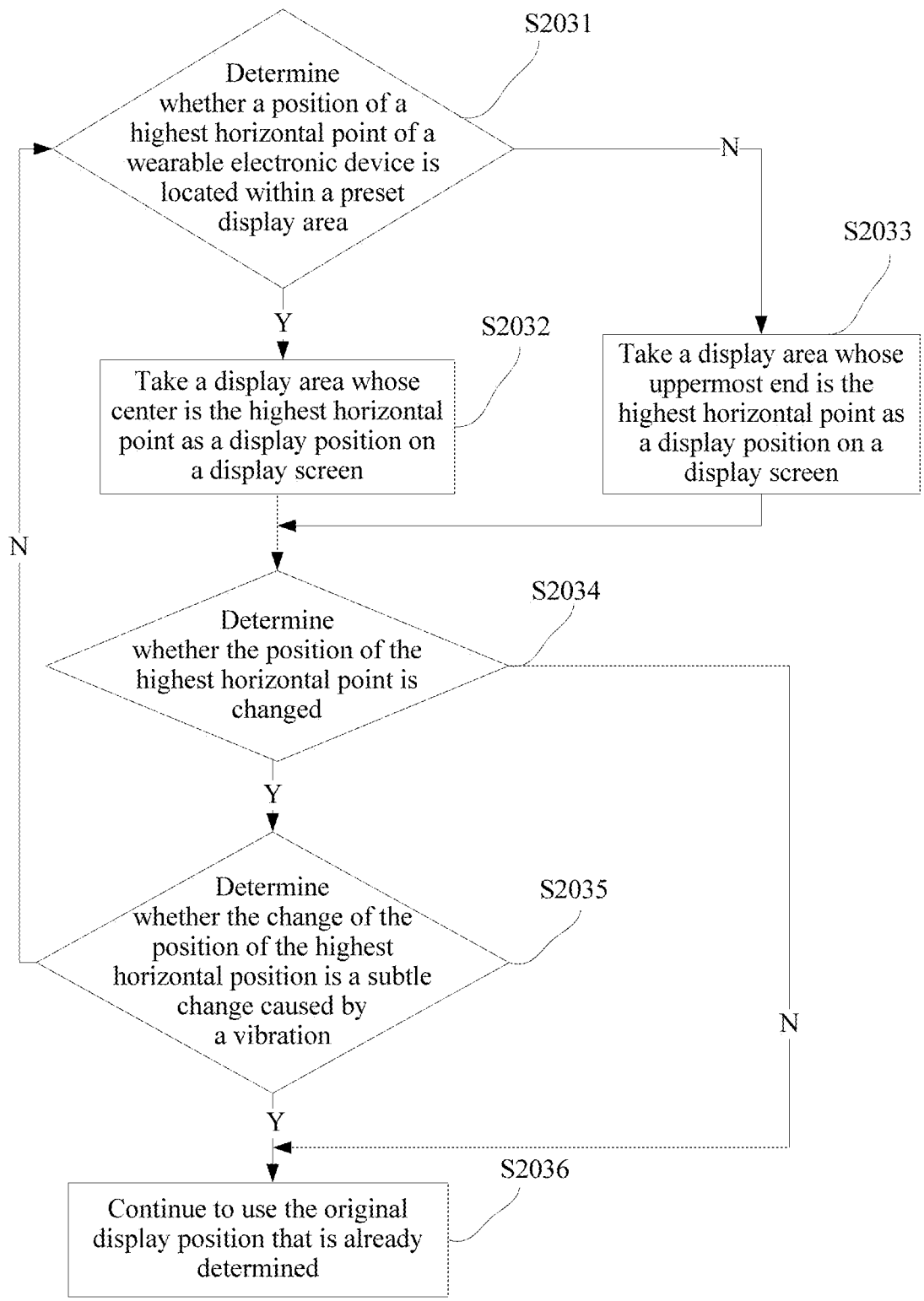
FIG. 5 is a schematic flowchart of determining a display position on a display screen according to an area, on a wearable device, in which a position of a highest horizontal point of the wearable electronic device is located according to an embodiment of the present disclosure.

In an embodiment, a specific implementation manner of determining the display position on the display screen according to the area, on the wearable device, in which the position of the highest horizontal point of the wearable electronic device is located may be determined using a process shown in FIG. 5.

S2031: Determine whether the position of the highest horizontal point of the wearable electronic device is located within a preset display area.

In this embodiment of the present disclosure, at least one display area may be preset on the display screen. When the position of the highest horizontal point of the electronic device is acquired, it may be determined whether the position of the highest horizontal point of the electronic device is located within the preset display area, if yes, S2032 is performed, if no, S2033 is performed.

S2032: Use a display area whose center is the highest horizontal point as the display position on the display screen.

S2033: Use a display area whose uppermost end is the highest horizontal point as the display position on the display screen.

Further, in this embodiment of the present disclosure, after the display position on the display screen is determined, the following steps may further be continued.

S2034: Determine whether the position of the highest horizontal position is changed, if the position of the highest horizontal position is changed, perform S2035, if the position of the highest horizontal position is not changed, perform S2036.

S2035: Determine whether the change of the position of the highest horizontal position is a subtle change caused by a vibration, if yes, perform S2036, if no, perform S2031 again to determine a display position again.

S2036: Continue to use the original display position determined in S2032 or S2033.

S204: Generate a display control signal that controls the display screen to display at the display position determined in S203, send the display control signal to a display controller 3, and instruct the display controller 3 to control the display screen to display at the display position determined in S203.

In this embodiment of the present disclosure, the sensor 1 is configured to collect device status data using a horizontal sensor or a gravity sensor, acquire a position of a highest horizontal point of the wearable electronic device, generate a sensor signal that represents the position of the highest horizontal point of the wearable electronic device, and send the sensor signal to the processor 2.

The processor 2 is configured to receive the sensor signal that represents the position of the highest horizontal point of the wearable electronic device and is sent by the horizontal sensor or the gravity sensor, determine a display position on a display screen according to an area, on the wearable electronic device, in which the position of the highest horizontal point of the wearable electronic device is located, generate a display control signal that controls the display screen to display at the display position, send the display control signal to the display controller 3, and instruct the display controller 3 to control the display screen to display at the display position.

Further, the processor 2 is configured to determine whether the position of the highest horizontal point of the wearable electronic device is located within a preset display area, and if yes, use a display area whose center is the highest horizontal point as the display position on the display screen, or if no, use a display area whose uppermost end is the highest horizontal point as the display position on the display screen.

Figure 6:
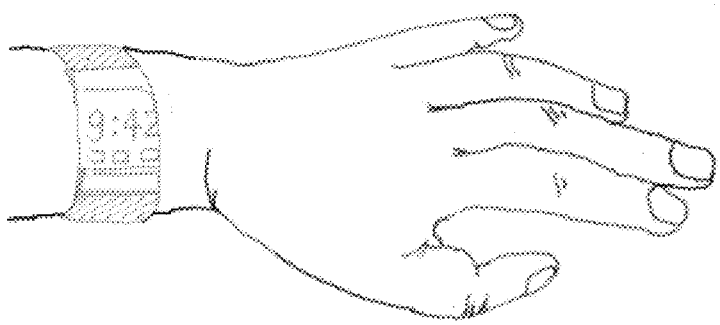
FIG. 6 is a schematic diagram of displaying related content by a wearable electronic device at a top of the device according to an embodiment of the present disclosure.

In this embodiment of the present disclosure, a position of a highest horizontal point of a wearable electronic device is determined using a horizontal sensor or a gravity sensor of a sensor module, and a display position on a display screen is determined according to the position of the highest horizontal point, the display position can be determined at an uppermost end of the wearable electronic device, and the uppermost end of the wearable electronic device is at a position at which time is displayed in FIG. 6, related content is displayed at the uppermost end of the wearable electronic device, which adapts to different wearing postures and can be more convenient for a user to view the related content.

Embodiment 3

In this embodiment of the present disclosure, to make it more convenient for a user to use a wearable electronic device, when a display screen of the wearable electronic device is in a standby state, an area around a tapping position may be automatically lighted according to operation data of the user, such as the tapping position of the user such that the user can perform an operation on the lighted area part.

In this embodiment of the present disclosure, a sensor 1 is set as a touch sensor, and a display 4 includes a display screen that is in a standby state. Operation data of the user can be collected using the touch sensor, and a tapping position of the user on the display screen that is in the standby state is acquired. The touch sensor generates a sensor signal that represents the acquired tapping position, and sends the sensor signal to a processor 2, and the sensor signal that represents the tapping position. The processor 2 receives touch sensor, determines, according to the current tapping position, a lighted area on the display screen that is in the standby state, and generates a display control signal that controls the display screen that is in the standby state to display the lighted area, and sends the display control signal to a display controller 3. The display controller 3 controls, according to the received display control signal, the display screen that is in the standby state to display the lighted area.

Figure 7:
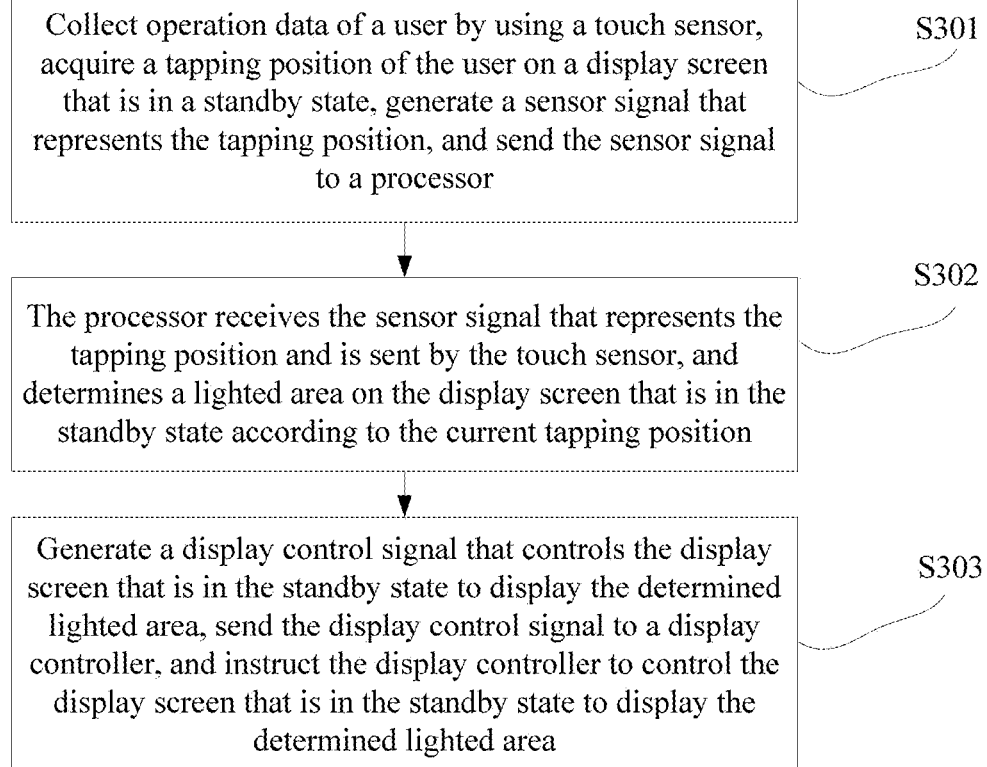
FIG. 7 is a schematic flowchart of determining a lighted area on a display screen based on a tapping position of a user according to an embodiment of the present disclosure.

In this embodiment of the present disclosure, a process of determining the lighted area on the display screen based on the tapping position of the user is shown in FIG. 7, and includes the following steps.

S301: Collect operation data of a user using a touch sensor, acquire a tapping position of the user on a display screen that is in a standby state, generate a sensor signal that represents the tapping position, and send the sensor signal to a processor 2.

S302: The processor 2 receives the sensor signal that represents the tapping position and is sent by the touch sensor, and determines, according to the current tapping position, a lighted area on the display screen that is in the standby state.

In an embodiment, the following manner may be preferably used in a process in which a sensor module in this embodiment of the present disclosure determines, according to a current electrode position, the lighted area on the display screen that is in the standby state.

Figure 8A:
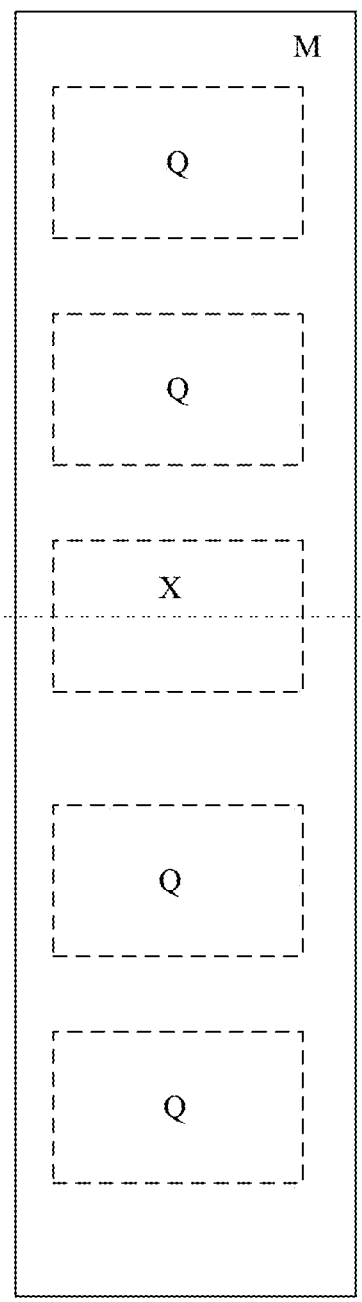
FIG. 8A to FIG. 8C are schematic diagrams of a process of determining a display position according to an embodiment of the present disclosure.

A: Divide in advance a display screen M that is in an electrode state from a center position X to two sides by a fixed display area size into several display sub-areas Qs as shown in FIG. 8A.

B: Determine whether the current tapping position is located within a display sub-area Q on the display screen that is in the standby state.

Figure 8B:
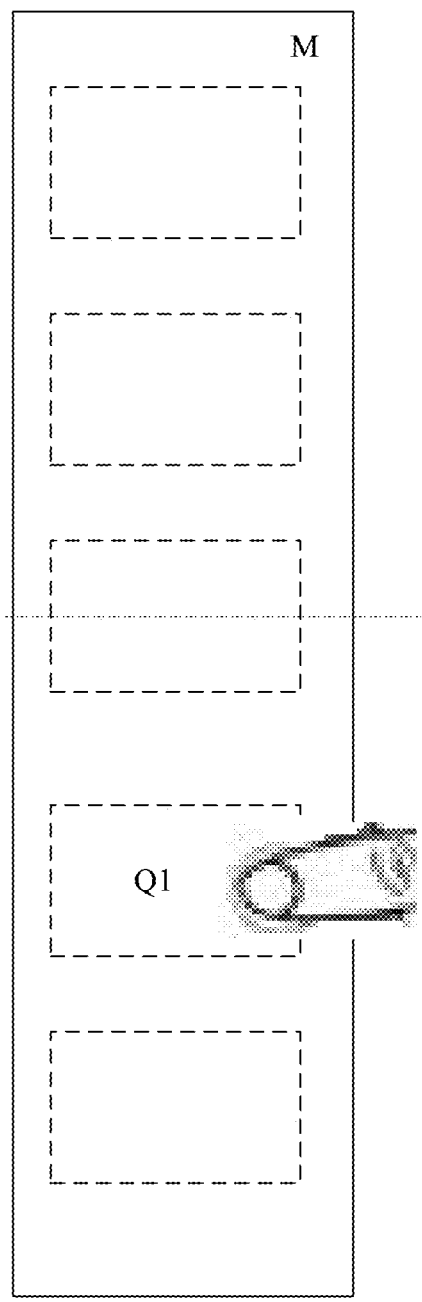

If yes, a display sub-area in which the current tapping position is located is used as the lighted area on the display screen that is in the standby state. As shown in FIG. 8B, if the tapping position is precisely located within a display sub-area Q1, the display sub-area Q1 is determined as the lighted area on the display screen that is in the standby state.

Figure 8C:
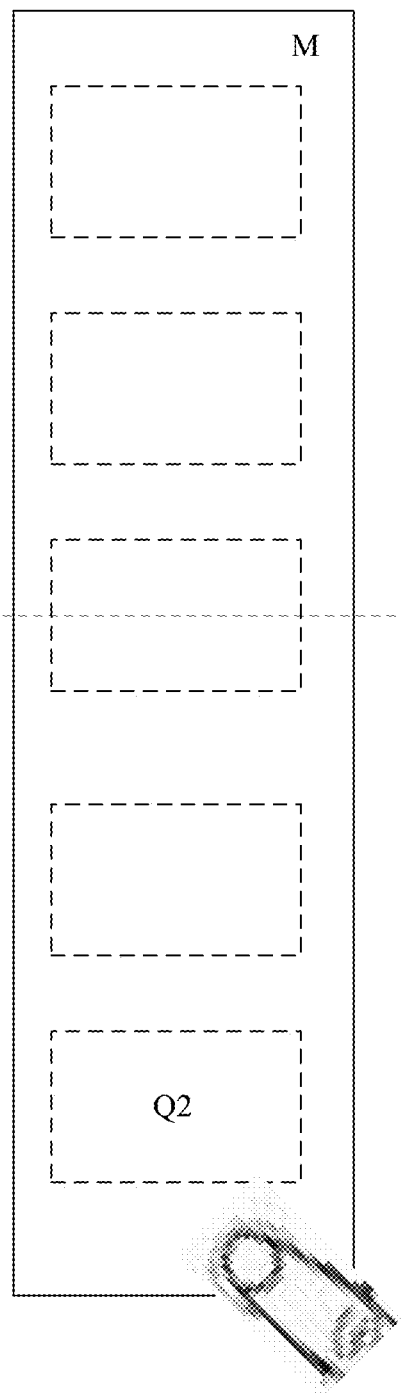

If no, a display sub-area adjacent to the current tapping position is used as the lighted area on the display screen that is in the standby state. As shown in FIG. 8C, if the tapping position is not located within any display sub-area, a display sub-area Q2 adjacent to the tapping position is used as the lighted area on the display screen that is in the standby state.

In the foregoing manner of determining the lighted area, a size of the lighted area may be determined with reference to a size of the display screen, which can adapt to the size of the display screen and helps to clearly display content.

S303: Generate a display control signal that controls the display screen that is in the standby state to display the lighted area determined in S302, send the display control signal to a display controller 3, and instruct the display controller 3 to control the display screen that is in the standby state to display the lighted area determined in S302.

In an embodiment, that the display controller 3 in this embodiment of the present disclosure controls the display screen that is in the standby state to display the determined lighted area may be implemented using the following manner.

If the user does not lock the screen, the display controller 3 invokes a power response event (screen-off/screen-on), supplies power to the determined lighted area, and controls the display to turn on backlight of the determined lighted area. A home screen is directly displayed in a determined area in which the screen needs to be lighted.

If the user locks the screen, the display controller 3 needs to first query a screen-locked state (locked/unlocked). If the screen is in a screen-locked state, after invoking a power response event (screen-off/screen-on), the display controller 3 supplies power to the determined lighted area, and controls to turn on backlight of the determined area. A lock screen is first displayed in a determined area in which a screen needs to be lighted, and after the user unlocks the screen, a home screen is displayed.

Further, in this embodiment of the present disclosure, when the lighted area is displayed, the following operation may further be performed on the lighted area to zoom in the display area zoom in, using the tapping position as a center, the lighted area outwards to a preset area range or an area range that adapts to a size of the display screen, or zoom in, using a horizontal line in which the tapping position is located as a top, the lighted area downwards to a preset area range or an area range that adapts to a size of the display screen, or zoom in, using a horizontal line in which the tapping position is located as a bottom, the lighted area upwards to a preset area range or an area range that adapts to a size of the display screen.

In an embodiment, an implementation process of zooming in display content in the lighted area in this embodiment of the present disclosure may be executed by a display. The present area range is an area range of a size that is not greater than the size of the display screen and that is preset by the user according to the size of the display screen. The area range that adapts to the size of the display screen is an area range lighted by means of automatically identifying the size of the display screen in a process of zooming in the lighted area. For example, if the size of the display screen is 10×20, the area range that adapts to the size of the display screen may be an area range adaptive to a size of 10×20, or may be an area range adaptive to a size of 10×10.

Figure 9:
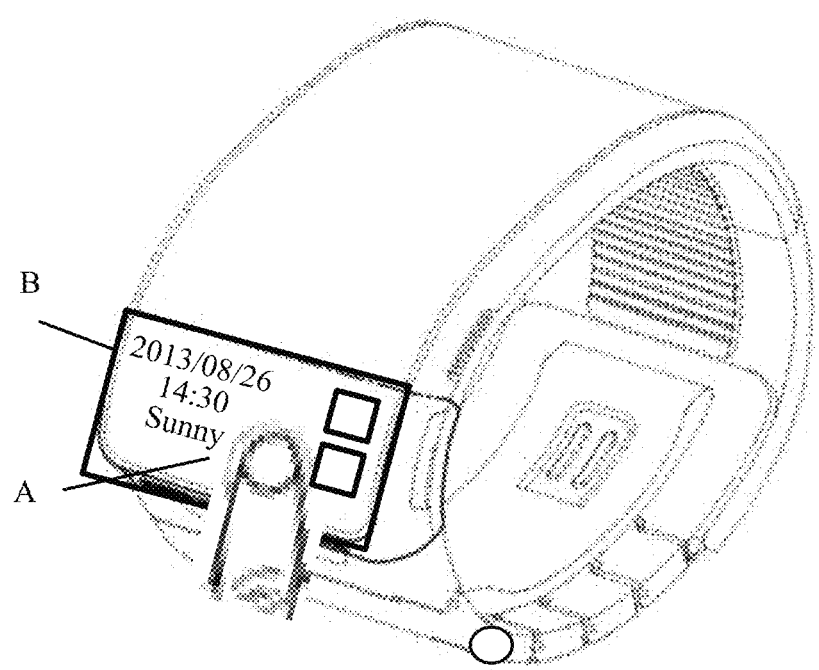
FIG. 9 is a schematic diagram of determining a lighted area on a display screen based on a tapping position of a user according to an embodiment of the present disclosure.

In this embodiment of the present disclosure, a lighted area on a display screen that is in a standby state can be determined according to a tapping position, the lighted area is displayed, and a display position on the display screen can be determined according to an operation of a user. For example, as shown in FIG. 9, the user may use an area B surrounding a tapping position A as the lighted area such that the display screen finally only displays the lighted area B to make it more convenient when the user views display content. In addition, display content in the lighted area may be displayed by means of zooming in such that the displayed content is more intuitive, which is convenient for the user to perform an operation.

Embodiment 4

In this embodiment of the present disclosure, corresponding processing may be performed on display content on a wearable electronic device to make it convenient for a user to view the display content.

In this embodiment of the present disclosure, a processor 2 may determine, according to a current application used on the wearable electronic device, an area of interest that a user intends to focus on or an operation area in which a user needs to perform an operation, then generate a full-screen display control signal for displaying in full screen the determined area of interest or operation area, and send the full-screen display control signal to a display controller 3. The display controller 3 controls a display to display in full screen the area of interest or the operation area.

In an embodiment, the current application used on the wearable electronic device in this embodiment of the present disclosure may be an application that is currently used on the wearable electronic device, or may be a related application that is associated with an application currently triggered by the user. For example, in this embodiment of the present disclosure, when there is a call, an icon for answering a call may be used as an operation area in which the user needs to perform an operation. In this case, the icon for answering a call is displayed in full screen such that only the icon for answering a call is displayed on an entire display screen, which is convenient for the user to tap. For another example, when the user selects a menu, an icon of each application associated with the menu may be used as the area of interest that the user intends to focus on, and the icon of each application is displayed in full screen such that the icon of each application occupies the entire display screen, and an application may be changed by sliding the screen up and down or left and right. When the user selects a contact, information of each contact may be used as the area of interest that the user intends to focus on, the information of each contact is displayed in full screen, and a contact may be changed by sliding the screen up and down or left and right. When audio or a video is played, a related control button is used as the operation area in which the user needs to perform an operation, and the related control button is semi-transparently displayed in full screen on an original screen. When the user browses a web page or a picture, the area of interest that the user intends to focus on is positioned according to a behavior (such as a gesture or a tap) of the user, and the area of interest is displayed in full screen, which is convenient for the user to tap and view related content.

Further, a display area may display a preconfigured home screen, such as time, calendar, and weather, or may display a shortcut menu, for example, an icon of an APP (application) that is relatively frequently used may be displayed, or an unlocking key may be displayed. In this embodiment of the present disclosure, a size of the display area on the display screen may be adjusted according to preconfigured display content (a quantity of icons or menus that are displayed on a home screen) to zoom in or zoom out the display area on the display screen, or certainly, a size of the display area on the display screen may be a default fixed size.

In this embodiment of the present disclosure, the processor 3 generates, according to frequency of actually using an APP, a display menu of the home screen by means of self-learning, and displays an icon of an APP that is relatively frequently used such that in the display area on the display screen, the size of the display area may be adjusted according to a quantity of icons of APPs that are actually used.

Figure 10:
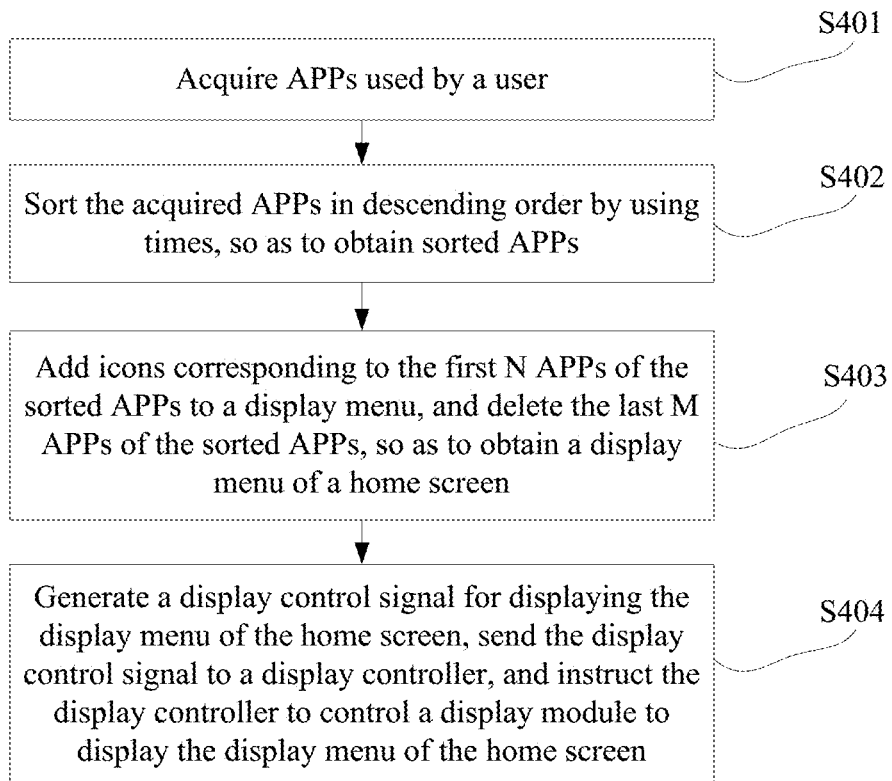
FIG. 10 is an implementation flowchart of generating a display menu of a home screen by means of self-learning according to an embodiment of the present disclosure.

In this embodiment of the present disclosure, the processor 3 may add an icon of an APP that is frequently used to the menu of the home screen, and deletes an icon of an APP that is not used in a long time from the display menu of the home screen to generate the display menu of the home screen by means of self-learning. An embodiment of an implementation process is shown in FIG. 10, and includes the following steps.

S401: Acquire APPs used by a user.

S402: Sort the acquired APPs in descending order by frequency of use to obtain sorted APPs.

S403: Add icons corresponding to the first N APPs of the sorted APPs to a display menu, and delete the last M APPs of the sorted APPs to obtain a display menu of a home screen.

S404: Generate a display control signal for displaying the display menu of the home screen, send the display control signal to a display controller, and instruct the display controller to control a display to display the display menu of the home screen.

In this embodiment of the present disclosure, on a wearable device, related content can be displayed according to a specific operation of a user. In addition, a manner to display has flexibility, which may be that the related display content is displayed in full screen and the display content is zoomed in, or may be that all content is displayed, or may be that partial content is displayed, and a display area can be adjusted according to the display content such that the display content is intuitive, which is convenient for the user to use the wearable device.

Embodiment 5

Figure 11:
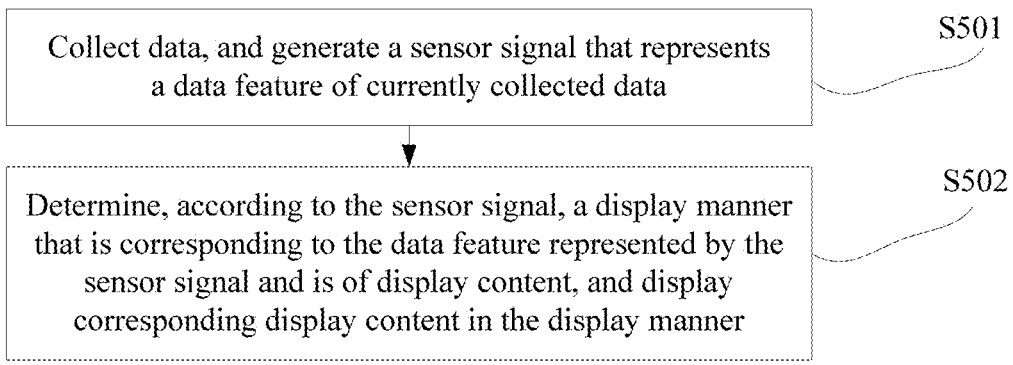
FIG. 11 to FIG. 16 are flowcharts of different display methods of a wearable electronic device according to an embodiment of the present disclosure.

Based on the foregoing provided wearable electronic device, Embodiment 5 of the present disclosure provides a display method of a wearable electronic device, and as shown in FIG. 11, the method includes the following steps.

S501: Collect data, and generate a sensor signal that represents a feature of data of currently collected data.

S502: Determine, according to the sensor signal generated in S501, a manner to display that is corresponding to the feature of data represented by the sensor signal and is of display content, and display corresponding display content in the manner to display.

In a first possible implementation manner, the collecting data, and generating a sensor signal that represents a feature of data of currently collected data includes collecting vital sign data of a user using a vital sign sensor, and generating a sensor signal that represents the vital sign data of the user, and the determining a manner to display that is corresponding to the feature of data represented by the sensor signal and is of display content, and displaying corresponding display content in the manner to display includes determining, according to a correspondence between a parameter level of vital sign data and a display color of an electrochromic housing, a color that is corresponding to the current vital sign data and should be displayed by the electrochromic housing, and generating a color display control signal, and controlling, according to the color display control signal, the electrochromic housing to display the color corresponding to the current vital sign data.

In a second possible implementation manner, before the determining a manner to display that is corresponding to the feature of data represented by the sensor signal and is of display content, the method further includes setting a correspondence between at least one different controllable electrochromic area included by the electrochromic housing and different types of vital sign data of the user, where different controllable electrochromic areas are corresponding to different types of vital sign data of the user.

In a third possible implementation manner, the collecting data, and generating a sensor signal that represents a feature of data of currently collected data includes collecting device status data using a horizontal sensor or a gravity sensor, acquiring a position of a highest horizontal point of a wearable electronic device, and generating a sensor signal that represents the position of the highest horizontal point of the wearable electronic device, and the determining a manner to display that is corresponding to the feature of data represented by the sensor signal and is of display content, and displaying corresponding display content in the manner to display includes determining a display position on a display screen according to an area, on the wearable electronic device, in which the position of the highest horizontal point of the wearable electronic device is located, generating a display control signal that controls the display screen to display at the display position, and controlling, according to the display control signal, the display screen to display the display content at the display position.

In a fourth possible implementation manner, the determining a display position on a display screen according to an area, on the wearable electronic device, in which the position of the highest horizontal point of the wearable electronic device is located includes determining whether the position of the highest horizontal point of the wearable electronic device is located within a preset display area, and if yes, using a display area whose center is the highest horizontal point as the display position on the display screen, or if no, using a display area whose uppermost end is the highest horizontal point as the display position on the display screen.

In a fifth possible implementation manner, the collecting data, and generating a sensor signal that represents a feature of data of currently collected data includes collecting operation data of a user using a touch sensor, acquiring a tapping position of the user on a display screen that is in a standby state, and generating a sensor signal that represents the tapping position, and the determining a manner to display that is corresponding to the feature of data represented by the sensor signal and is of display content, and displaying corresponding display content in the manner to display includes determining, according to the current tapping position, a lighted area on the display screen that is in the standby state, generating a display control signal that controls the display screen that is in the standby state to display the lighted area, and controlling, according to the display control signal, the display screen that is in the standby state to display the lighted area.

In a sixth possible implementation manner, the determining, according to the current tapping position, a lighted area on the display screen that is in the standby state includes determining whether the current tapping position is located within a display sub-area that is obtained by dividing the display screen that is in the standby state from the center to two sides by a fixed display area size, and if yes, using a display sub-area in which the current tapping position is located as the lighted area, or if no, using a display sub-area adjacent to the current tapping position as the lighted area.

In a seventh possible implementation manner, after the determining a lighted area on the display screen that is in the standby state, the method further includes zooming in, using the tapping position as a center, the lighted area outwards to a preset area range or an area range that adapts to a size of the display screen, or zooming in, using a horizontal line in which the tapping position is located as a top, the lighted area downwards to a preset area range or an area range that adapts to a size of the display screen, or zooming in, using a horizontal line in which the tapping position is located as a bottom, the lighted area upwards to a preset area range or an area range that adapts to a size of the display screen.

In an eighth possible implementation manner, the determining a manner to display that is corresponding to the feature of data represented by the sensor signal and is of display content, and displaying corresponding display content in the manner to display includes determining, according to a current application used on a wearable electronic device, an area of interest that a user intends to focus on or an operation area in which a user needs to perform an operation, generating a full-screen display control signal for displaying in full screen the area of interest or the operation area, and displaying in full screen the area of interest or the operation area according to the full-screen display control signal.

In a ninth possible implementation manner, the determining a manner to display that is corresponding to the feature of data represented by the sensor signal and is of display content, and displaying corresponding display content in the manner to display includes acquiring applications APPs used by a user, and sorting the APPs in descending order by frequency of use to obtain sorted APPs, adding icons corresponding to the first N APPs of the sorted APPs to a display menu, and deleting the last M APPs of the sorted APPs to obtain a display menu of a home screen, generating a display control signal for displaying the display menu of the home screen, and displaying the display menu of the home screen according to the display control signal.

For various display methods provided in this embodiment of the present disclosure, reference may be made to Embodiment 1 to Embodiment 4 again.

According to the display method of a wearable electronic device that is provided in this embodiment of the present disclosure, data is collected using a sensor, and a sensor signal that represents a feature of data is transmitted to a processor, the processor can determine, according to the received sensor signal, a manner to display that is corresponding to the feature of data represented by the sensor signal, and generate a display control signal, and a display controller controls, according to the display control signal, a display to display correspondingly. That is, in the present application, different manner to displays can be determined according to different feature of datas, and a manner to display has flexibility, for example, a color corresponding to current vital sign data may be displayed using an electrochromic housing, or corresponding display content may be displayed at a highest point of the wearable device such that a user can view clearly and easily display content related to a current feature of data.

Embodiment 6

Figure 12:
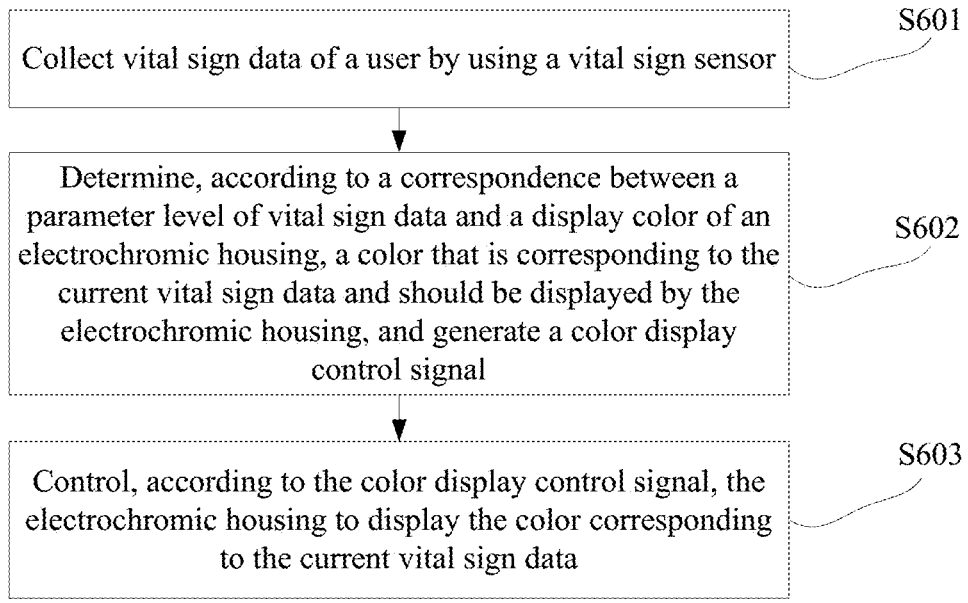

Embodiment 6 of the present disclosure provides a method for displaying vital sign data by a wearable electronic device, and as shown in FIG. 12, the method includes the following steps.

S601: Collect vital sign data of a user using a vital sign sensor.

S602: Determine, according to a correspondence between a parameter level of vital sign data and a display color of an electrochromic housing, a color that is corresponding to the current vital sign data and should be displayed by the electrochromic housing, and generate a color display control signal.

S603: Control, according to the color display control signal, the electrochromic housing to display the color corresponding to the current vital sign data.

In a first possible implementation manner, before the determining a manner to display that is corresponding to the feature of data represented by the sensor signal and is of display content, the method further includes setting a correspondence between at least one different controllable electrochromic area included by the electrochromic housing and different types of vital sign data of the user, where different controllable electrochromic areas are corresponding to different types of vital sign data of the user.

For an implementation process of displaying corresponding vital sign data using the electrochromic housing of the wearable electronic device in this embodiment of the present disclosure, reference may be made to FIG. 3.

In this embodiment of the present disclosure, different control signals are generated according to different feature data of a user who wears the wearable electronic device to control an electrochromic housing of the wearable electronic device to display different colors, and different colors represent different vital sign data, that is, different health statuses. Wearers may directly learn their own physical condition according to a color displayed by the housing of the wearable electronic device.

Embodiment 7

Figure 13:
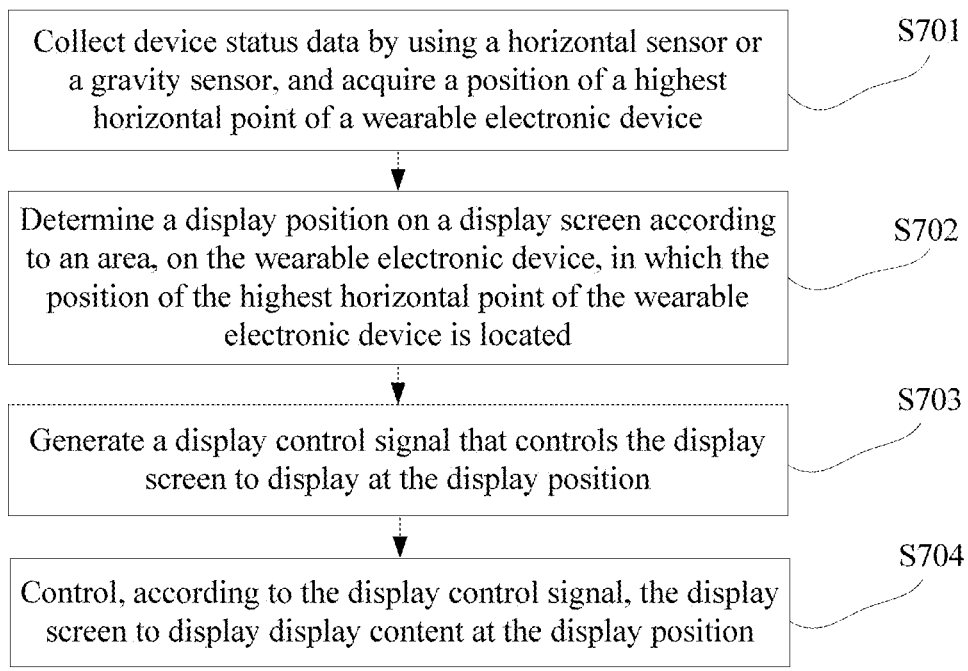

Embodiment 7 of the present disclosure provides a display method of a wearable electronic device, and as shown in FIG. 13, the method includes the following steps.

S701: Collect device status data using a horizontal sensor or a gravity sensor, and acquire a position of a highest horizontal point of a wearable electronic device.

S702: Determine a display position on a display screen according to an area, on the wearable electronic device, in which the position of the highest horizontal point of the wearable electronic device is located.

S703: Generate a display control signal that controls the display screen to display at the display position.

S704: Control, according to the display control signal, the display screen to display content at the display position.

In a first possible implementation manner, the determining a display position on a display screen according to an area, on the wearable electronic device, in which the position of the highest horizontal point of the wearable electronic device is located includes determining whether the position of the highest horizontal point of the wearable electronic device is located within a preset display area, and if yes, using a display area whose center is the highest horizontal point as the display position on the display screen, or if no, using a display area whose uppermost end is the highest horizontal point as the display position on the display screen.

In this embodiment of the present disclosure, for a process of determining the display position on the display screen, reference may be made to FIG. 4 again.

In this embodiment of the present disclosure, a position of a highest horizontal point of a wearable electronic device is determined using a horizontal sensor or a gravity sensor of a sensor module, a display position on a display screen is determined according to the position of the highest horizontal point, the display position can be determined at an uppermost end of the wearable electronic device, and related content is displayed at the uppermost end of the wearable electronic device, which adapts to different wearing postures and can be more convenient for a user to view the related content.

Embodiment 8

Figure 14:
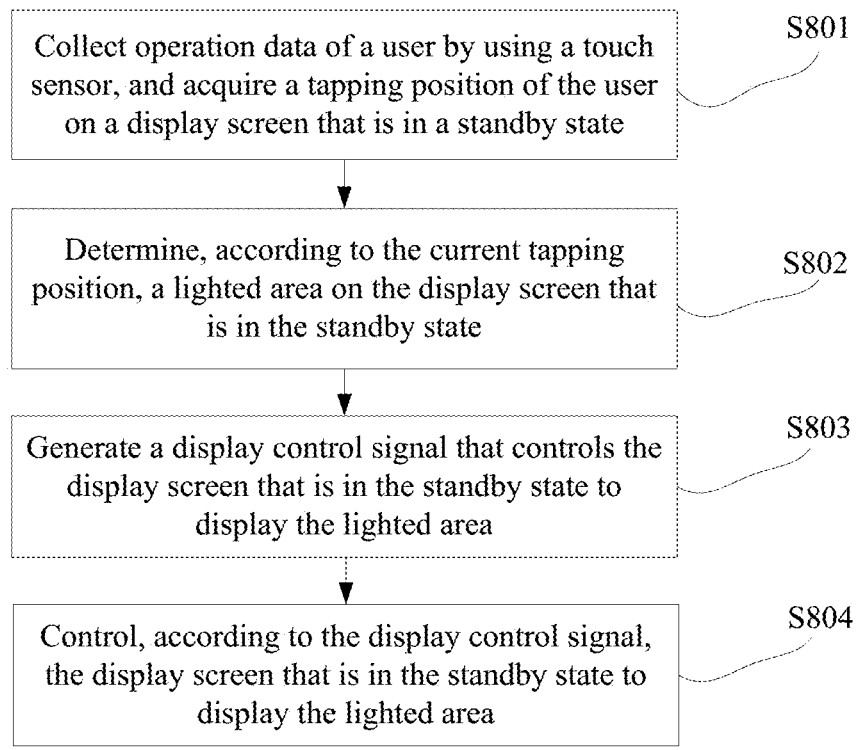

Embodiment 8 of the present disclosure provides a display method of a wearable electronic device, and as shown in FIG. 14, the method includes the following steps.

S801: Collect operation data of a user using a touch sensor, and acquire a tapping position of the user on a display screen that is in a standby state.

S802: Determine, according to the current tapping position, a lighted area on the display screen that is in the standby state.

S803: Generate a display control signal that controls the display screen that is in the standby state to display the lighted area.

S804: Control, according to the display control signal, the display screen that is in the standby state to display the lighted area.

In a first possible implementation manner, the determining, according to the current tapping position, a lighted area on the display screen that is in the standby state includes determining whether the current tapping position is located within a display sub-area that is obtained by dividing the display screen that is in the standby state from the center to two sides by a fixed display area size, and if yes, using a display sub-area in which the current tapping position is located as the lighted area, or if no, using a display sub-area adjacent to the current tapping position as the lighted area.

In a second possible implementation manner, after the determining a lighted area on the display screen that is in the standby state, the method further includes zooming in, using the tapping position as a center, the lighted area outwards to a preset area range or an area range that adapts to a size of the display screen, zooming in, using a horizontal line in which the tapping position is located as a top, the lighted area downwards to a preset area range or an area range that adapts to a size of the display screen, or zooming in, using a horizontal line in which the tapping position is located as a bottom, the lighted area upwards to a preset area range or an area range that adapts to a size of the display screen.

For implementation manners of Embodiment 8 of the present disclosure, reference may be made to FIG. 7 again.

In this embodiment of the present disclosure, a lighted area on a display screen that is in a standby state can be determined according to a tapping position, the lighted area is displayed, and a display position on the display screen can be determined according to an operation of a user to make it more convenient when the user views display content. In addition, display content in the lighted area may be displayed by means of zooming in such that the display content is more intuitive, which is convenient for the user to perform an operation.

Embodiment 9

Figure 15:
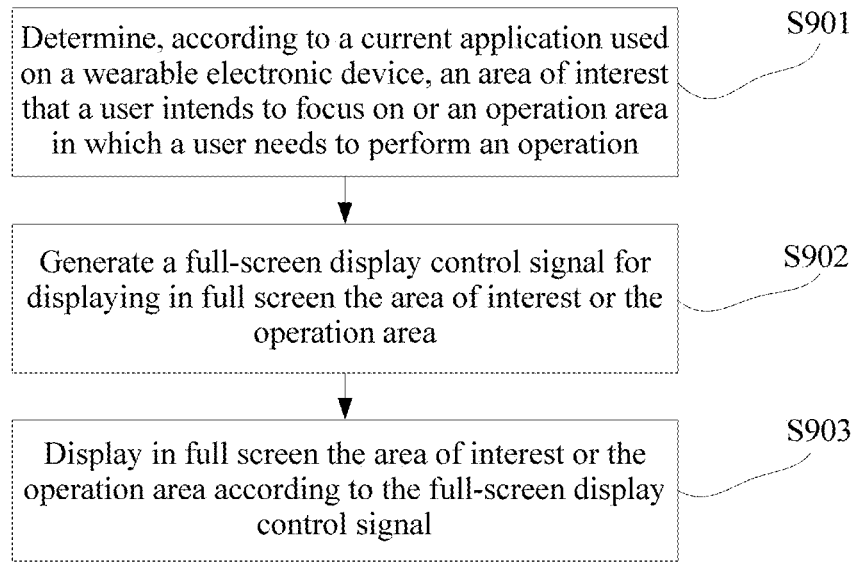

Embodiment 9 of the present disclosure provides a display method of a wearable electronic device, and as shown in FIG. 15, the method includes the following steps.

S901: Determine, according to a current application used on a wearable electronic device, an area of interest that a user intends to focus on or an operation area in which a user needs to perform an operation.

S902: Generate a full-screen display control signal for displaying in full screen the area of interest or the operation area.

S903: Display in full screen the area of interest or the operation area according to the full-screen display control signal.

In this embodiment of the present disclosure, an area of interest that a user intends to focus on or an operation area in which a user needs to perform an operation is determined according to a current application used on a wearable electronic device, and the area of interest and the operation area are displayed in full screen, which is more convenient for the user to view related content.

In this embodiment of the present disclosure, on a wearable device, related content can be displayed according to a specific operation of a user. In addition, a manner to display has flexibility, which may be that the related display content is displayed in full screen and the display content is zoomed in, or may be that all content is displayed, or may be that partial content is displayed, and a display area can be adjusted according to the display content such that the display content is intuitive, which is convenient for the user to use the wearable device.

Embodiment 10

Figure 16:
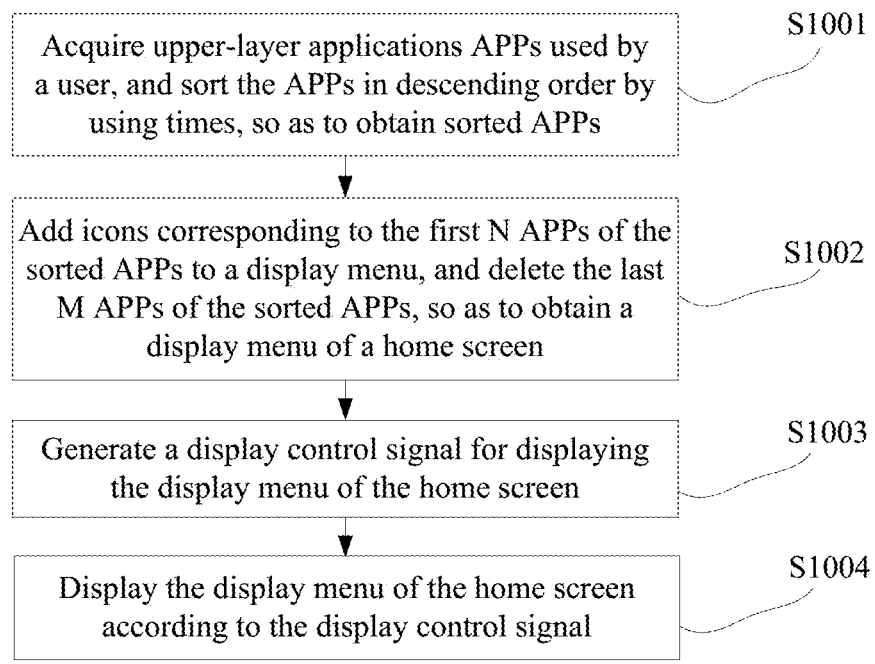

Embodiment 10 of the present disclosure provides a display method of a wearable electronic device, and as shown in FIG. 16, the method includes the following steps.

S1001: Acquire applications APPs used by a user, and sort the APPs in descending order by frequency of use to obtain sorted APPs.

S1002: Add icons corresponding to the first N APPs of the sorted APPs to a display menu, and delete the last M APPs of the sorted APPs to obtain a display menu of a home screen.

S1003: Generate a display control signal for displaying the display menu of the home screen.

S1004: Display the display menu of the home screen according to the display control signal.

For an implementation process of this embodiment of the present disclosure, reference may be made to FIG. 10 again.

In this embodiment of the present disclosure, based on frequency of APP use by a user, a display menu that is of a home screen and consists of icons of APPs that are relatively frequently used is displayed, which can be more convenient for a user to perform an operation and view the icons.

Embodiment 11

Figure 17:
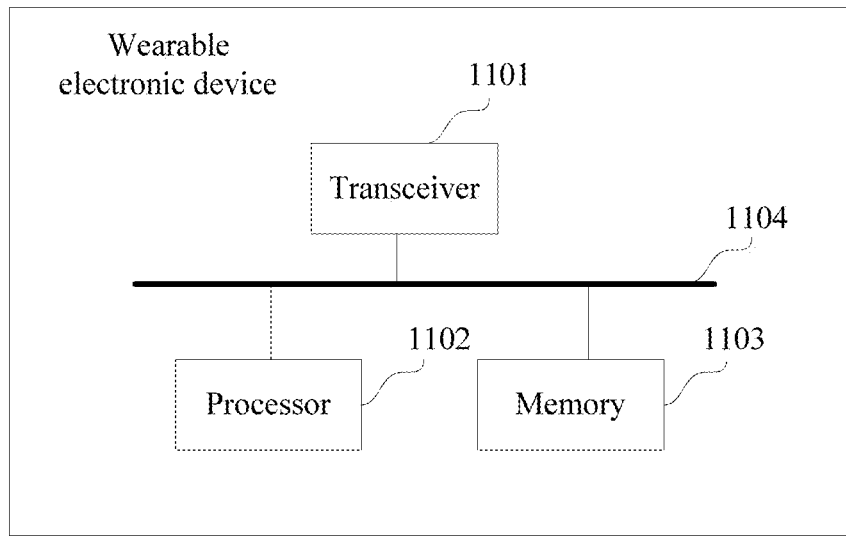
FIG. 17 is another schematic diagram of composition of a wearable electronic device according to an embodiment of the present disclosure.

Embodiment 11 of the present disclosure further provides a wearable electronic device. As shown in FIG. 17, the apparatus includes a transceiver 1101, a processor 1102, a memory 1103, and a bus 1104, where the transceiver 1101, the processor 1102, and the memory 1103 are all connected to the bus 1104.

The processor 1102 is configured to acquire, using the transceiver 1101, data collected by a sensor, generates a sensor signal that represents a feature of data of the currently collected data, determine, according to the sensor signal, a manner to display that is corresponding to the feature of data represented by the sensor and is of display content, and display corresponding display content in the manner to display.

The processor 1102 completes execution of the foregoing process generally under control of one or more software programs, where the foregoing one or more software programs are stored in the memory 1103. When the processor 1102 needs to execute the foregoing process, he foregoing one or more software programs are invoked by the processor 1102, and the foregoing process is completed under control of the processor 1102. Certainly, execution of the foregoing process by the processor 1102 may also be implemented using hardware, and this embodiment of the present disclosure sets no limitation.

The wearable electronic device provided in this embodiment of the present disclosure may be configured to execute an implementation process involved in any one of the foregoing embodiments, and details are not described herein again. For descriptions that are of execution functions of the wearable electronic device involved in this embodiment of the present disclosure and are not given in detail, reference may be made to Embodiment 1 to Embodiment 10 again.

According to the wearable electronic device provided in this embodiment of the present disclosure, data is collected using a sensor, and a sensor signal that represents a feature of data is transmitted to a processor, the processor can determine, according to the received sensor signal, a manner to display that is corresponding to the feature of data represented by the sensor signal, and generate a display control signal, and a display controller controls, according to the display control signal, a display to display correspondingly. That is, in the present application, different manner to displays can be determined according to different feature of datas, and a manner to display has flexibility, for example, a color corresponding to current vital sign data may be displayed using an electrochromic housing, or corresponding display content may be displayed at a highest point of the wearable device such that a user can view clearly and easily display content related to a current feature of data.

Persons skilled in the art should understand that the embodiments of the present disclosure may be provided as a method, a system, or a computer program product. Therefore, the present disclosure may use a form of hardware only embodiments, software only embodiments, or embodiments with a combination of software and hardware. Moreover, the present disclosure may use a form of a computer program product that is implemented on one or more computer-usable storage media (including but not limited to a disk memory, a compact disc read only memory (CD-ROM), an optical memory, and the like) that include computer-usable program code.

The present disclosure is described with reference to the flowcharts and/or block diagrams of the method, the device (system), and the computer program product according to the embodiments of the present disclosure. It should be understood that computer program instructions may be used to implement each process and/or each block in the flowcharts and/or the block diagrams and a combination of a process and/or a block in the flowcharts and/or the block diagrams. These computer program instructions may be provided for a general-purpose computer, a dedicated computer, an embedded processor, or a processor of any other programmable data processing device to generate a machine such that the instructions executed by a computer or a processor of any other programmable data processing device generate an apparatus for implementing a specific function in one or more processes in the flowcharts and/or in one or more blocks in the block diagrams.

These computer program instructions may also be stored in a computer readable memory that can instruct the computer or any other programmable data processing device to work in a specific manner such that the instructions stored in the computer readable memory generate an artifact that includes an instruction apparatus. The instruction apparatus implements a specific function in one or more processes in the flowcharts and/or in one or more blocks in the block diagrams.

These computer program instructions may also be loaded onto a computer or another programmable data processing device such that a series of operations and steps are performed on the computer or the another programmable device, thereby generating computer-implemented processing. Therefore, the instructions executed on the computer or the another programmable device provide steps for implementing a specific function in one or more processes in the flowcharts and/or in one or more blocks in the block diagrams.

Although some preferred embodiments of the present disclosure have been described, persons skilled in the art can make changes and modifications to these embodiments once they learn the basic inventive concept. Therefore, the following claims are intended to be construed as to cover the preferred embodiments and all changes and modifications falling within the scope of the present disclosure.

Obviously, persons skilled in the art can make various modifications and variations to the embodiments of the present disclosure without departing from the spirit and scope of the embodiments of the present disclosure. The present disclosure is intended to cover these modifications and variations provided that they fall within the scope of protection defined by the following claims and their equivalent technologies.

What is claimed is:
1. A wearable electronic device, comprising:
a sensor configured to:
  collect data;
  generate a sensor signal that represents a feature of the data;
  collect device status data; and
  acquire a position of a highest horizontal point of the wearable electronic device, wherein the sensor signal represents the position of the highest horizontal point of the wearable electronic device, and wherein the sensor is a horizontal sensor or a gravity sensor;
a memory;
a processor coupled to the sensor and the memory, wherein the processor is configured to:
  receive, from a user, a range of features and a manner by which to display content that corresponds to the range of features;
  set a correspondence between the range of features and the manner by which to display the content that corresponds to the range of features;

determine whether the position of the highest horizontal point of the wearable electronic device is located within a preset display area;
determine the manner by which to display the content that corresponds to the feature of the data based on the correspondence when the range of features includes the feature of the data; and
determine a display position on the display screen according to an area on the wearable electronic device in which the position of the highest horizontal point of the wearable electronic device is located;
generate a display control signal that controls the display screen to display at the display position; and
control the display screen to display the content at the display position according to the display control signal;
a display screen coupled to the processor and configured to:
display the content based on the manner by which to display the data; and
use a display area with a center being the highest horizontal point as the display position on the display screen in response to the position of the highest horizontal point of the wearable electronic device being located within the preset display area.

2. The wearable electronic device of claim 1, wherein the processor is further configured to determine whether the position of the highest horizontal point of the wearable electronic device is located within a preset display area, and wherein the display screen is further configured to use a display area with an uppermost end being the highest horizontal point as the display position on the display screen in response to if the position of the highest horizontal point of the wearable electronic device not being located within the preset display area.

3. A wearable electronic device, comprising:
a sensor configured to:
collect data;
generate a sensor signal that represents a feature of the data;
collect operation data of a user; and
acquire a tapping position of the user on the display screen that is in a standby state, wherein the sensor signal represents the tapping position, and wherein the sensor is a touch sensor;
a memory;
a processor coupled to the sensor and the memory, wherein the processor is configured to:
receive, from the user, a range of features and a manner by which to display content that corresponds to the range of features;
set a correspondence between the range of features and the manner by which to display the content that corresponds to the range of features;
determine a lighted area on the display screen according to the tapping position;
generate a display control signal that controls the display screen to display the lighted area;
control the display screen to display the lighted area according to the display control signal;
divide the display screen that is in the standby state from a center to two sides by a fixed display area size to obtain a display sub-area;
determine whether the tapping position is located within a display sub-area on the display screen; and
determine the manner by which to display the content that corresponds to the feature of the data based on the correspondence when the range of features includes the feature of the data; and
a display screen coupled to the processor and configured to:
display the content based on the manner by which to display the data; and
use the display sub-area in which the tapping position is located as the lighted area in response to the tapping position being located within the display sub-area on the display screen that is in the standby state.

4. The wearable electronic device of claim 3, wherein the processor is further configured to zoom in the lighted area outwards to a preset area range or an area range that adapts to a size of the display screen using the tapping position as a center.

5. The wearable electronic device of claim 3, wherein the processor is further configured to zoom in the lighted area downwards to a preset area range or an area range that adapts to a size of the display screen using a horizontal line in which the tapping position is located as a top.

6. The wearable electronic device of claim 3, wherein the processor is further configured to zoom in the lighted area upwards to a preset area range or an area range that adapts to a size of the display screen by using a horizontal line in which the tapping position is located as a bottom.

7. The wearable electronic device of claim 3, wherein the processor is further configured to;
divide the display screen that is in the standby state from a center to two sides by a fixed display area size to obtain a display sub-area; and
determine whether the tapping position is located within a display sub-area on the display screen, wherein the display screen is further configured to use a display sub-area adjacent to the tapping position as the lighted area if the tapping position is located within the display sub-area on the display screen that is not in the standby state.

* * * * *